US009345605B2

(12) United States Patent
Dunn et al.

(10) Patent No.: US 9,345,605 B2
(45) Date of Patent: May 24, 2016

(54) HINGE FOR AN ORTHOPEDIC DEVICE

(71) Applicant: OSSUR HF, Reykjavik (IS)

(72) Inventors: Adam Dunn, Irvine, CA (US); Jane Lee, Fullerton, CA (US)

(73) Assignee: OSSUR HF, Reykjavik (IS)

( * ) Notice: Subject to any disclaimer, the term of this patent is extended or adjusted under 35 U.S.C. 154(b) by 350 days.

(21) Appl. No.: 13/905,478

(22) Filed: May 30, 2013

(65) Prior Publication Data
US 2013/0331754 A1     Dec. 12, 2013

Related U.S. Application Data

(60) Provisional application No. 61/653,507, filed on May 31, 2012, provisional application No. 61/657,288, filed on Jun. 8, 2012.

(51) Int. Cl.
*A61F 5/01*     (2006.01)

(52) U.S. Cl.
CPC ............... *A61F 5/01* (2013.01); *A61F 5/0123* (2013.01); *A61F 2005/0144* (2013.01); *A61F 2005/0167* (2013.01)

(58) Field of Classification Search
CPC .......... A61F 5/00; A61F 5/01; A61F 5/0102; A61F 5/0123; E05D 3/00; E05D 3/06; E05D 3/14
See application file for complete search history.

(56) References Cited

U.S. PATENT DOCUMENTS

| 3,901,223 | A | | 8/1975 | May |
| 4,723,539 | A | | 2/1988 | Townsend |
| 4,821,707 | A | | 4/1989 | Audette |
| 4,856,501 | A | * | 8/1989 | Castillo et al. .................. 602/16 |
| 4,886,054 | A | * | 12/1989 | Castillo et al. .................. 602/26 |
| 4,890,607 | A | | 1/1990 | Townsend |
| 4,940,044 | A | | 7/1990 | Castillo |

(Continued)

FOREIGN PATENT DOCUMENTS

| EP | 0454186 A2 | 10/1991 |
| EP | 0546330 A1 | 6/1993 |

(Continued)

OTHER PUBLICATIONS

International Search Report and Written Opinion, PCT/US2013/043322, Aug. 20, 2013.

(Continued)

*Primary Examiner* — Nicholas Woodall
*Assistant Examiner* — Raymond E Harris
(74) *Attorney, Agent, or Firm* — Workman Nydegger

(57) ABSTRACT

A hinge for an orthopedic device includes an upper hinge component, a lower hinge component, a first plate pivotally connected at a first location point to the upper hinge component and connected at a second location point to the lower hinge component, and a second plate pivotally connected at the first location point to the upper hinge component and at the second location point to the lower hinge component. A first rotation stop is connected at a third location point to the first and second plates. A center link is pivotally attached at a fourth location point to the upper hinge component and at a fifth location point to the lower hinge component. The center link has a first stop surface arranged to directly abut the first rotation stop. The hinge components and the center link are arranged between the first plate and the second plate.

20 Claims, 5 Drawing Sheets

(56) References Cited

U.S. PATENT DOCUMENTS

| | | | |
|---|---|---|---|
| 4,961,416 A | 10/1990 | Moore et al. | |
| 5,022,391 A | 6/1991 | Weidenburner | |
| 5,038,763 A | 8/1991 | Wiggins | |
| 5,168,865 A | 12/1992 | Radcliffe et al. | |
| 5,259,832 A | 11/1993 | Townsend | |
| 5,288,287 A | 2/1994 | Castillo et al. | |
| 5,356,370 A * | 10/1994 | Fleming | 602/16 |
| 5,372,572 A | 12/1994 | Tamagni | |
| 5,376,134 A * | 12/1994 | Biedermann | 623/39 |
| 5,490,822 A * | 2/1996 | Biedermann | 602/16 |
| 5,741,221 A | 4/1998 | Wetz et al. | |
| 6,074,355 A | 6/2000 | Bartlett | |
| 6,740,054 B2 | 5/2004 | Stearns | |
| 7,044,925 B2 | 5/2006 | Castillo et al. | |
| 7,059,329 B2 | 6/2006 | Mason et al. | |
| 7,235,058 B2 | 6/2007 | Doty et al. | |
| 7,507,215 B2 | 3/2009 | Ryan | |
| 7,534,219 B2 | 5/2009 | Stearns | |
| 7,544,174 B2 | 6/2009 | Nathanson | |
| 7,578,799 B2 | 8/2009 | Thorsteinsson et al. | |
| 7,762,972 B2 | 7/2010 | Cho | |
| 7,985,193 B2 | 7/2011 | Thorsteinsson et al. | |
| 8,287,476 B2 | 10/2012 | Bettiol | |
| 2005/0148915 A1 * | 7/2005 | Nathanson et al. | 602/16 |
| 2005/0192523 A1 | 9/2005 | Knecht et al. | |
| 2006/0009722 A1 | 1/2006 | Seligman | |
| 2006/0173392 A1 | 8/2006 | Turrini et al. | |
| 2008/0108922 A1 | 5/2008 | Castillo et al. | |
| 2008/0188784 A1 * | 8/2008 | Ceriani et al. | 602/16 |
| 2009/0030356 A1 | 1/2009 | Maloney | |
| 2009/0182254 A1 | 7/2009 | Cho | |
| 2009/0299244 A1 * | 12/2009 | Chiang et al. | 602/26 |
| 2010/0286579 A1 | 11/2010 | Bettiol | |
| 2012/0059296 A1 * | 3/2012 | Kompa | 602/16 |
| 2012/0271211 A1 * | 10/2012 | Bledsoe | 602/16 |
| 2013/0331754 A1 | 12/2013 | Dunn et al. | |

FOREIGN PATENT DOCUMENTS

| | | |
|---|---|---|
| WO | 90/14807 A1 | 12/1990 |
| WO | 2004/078078 A1 | 9/2004 |
| WO | 2009092798 A1 | 7/2009 |

OTHER PUBLICATIONS

International Search Report from International Application No. PCT/US2015/015358, Apr. 22, 2015.

* cited by examiner

HINGE FOR AN ORTHOPEDIC DEVICE

FIELD OF THE DISCLOSURE

The present disclosure relates to orthopedic devices, and more specifically to a hinge for an orthopedic device.

BACKGROUND

Many orthopedic devices include hinges that support joints, and control and limit joint movements. These joints include the knee, elbow, shoulder, hip, ankle and wrist joints.

The knee joint comprises two joints, lateral and medial, between the femur and tibia, and one arthrodial joint between the patella and femur. The primary movements of the knee comprise flexion (i.e., rearward rotational movement of the tibia relative the femur), and extension (i.e., forward rotational movement of the tibia relative the femur).

The flexion and extension movements of the knee joint are not pivotal movements about a fixed axis. During flexion, the axis around which movement takes place shifts backward, and during extension it shifts forward. This differs from a more typical hinge joint, such as an elbow, where the axis of rotation does not shift. As full extension is reached, the tibia is rotated inward or rearward, and the joint is disposed in a "locked" position with the ligaments taut. This gives the joint greater stability in the extended position. As flexion is initiated, the tibia initially lowers or moves downwardly with small external rotation of the tibia unlocking the joint and subsequently the tibia rotates or rolls about the joint to full flexion. The initial unlocking of the knee joint during flexion precedes actual full rotation of the knee.

Because of the complexity associated with knee movement a knee brace hinge must be able to simulate the movements of the knee. Incorporating such hinge is crucial, as the knee brace must optimally support the knee joint of its user.

In postsurgical applications, the requirement for such simulation of the knee joint is essential to rehabilitate and prevent re-injury of an injured knee joint. The hinge should also control the range of the knee joint flexion and extension so the knee is not reinjured due to hyperextension or flexion. As the optimal range of knee joint motion may vary between users and change during the progress of rehabilitation, the hinge used with such surgical applications should further be adjustable to correspond to the motion range of the user's leg.

In recognizing the need for an effective postsurgical knee brace, various types of hinges have been incorporated into known knee braces for postsurgical applications. However, most conventional hinges typically fail to provide the precise simulation of knee joint movement or control the range of knee joint motion. Such deficiencies inevitably decrease the user's knee joint being properly rehabilitated after surgery. Further, some known hinges fail to possess sufficient adjustability to provide, quickly and easily, the optimal set range of knee motion depending upon the current user's needs and rehabilitation progress.

In view of the shortcomings of conventional knee brace hinges. There exists a substantial need in the art for a hinge that can closely simulate the motion of the knee joint while regulating the range of its flexion and extension. It is desirable to provide a hinge that can be easily and quickly adjusted to provide a variable, optimal range of knee joint flexion and extension for the need of its user.

Many contemporary knee braces fail to provide the precise simulation of knee joint movement or have comprised relatively heavy, bulky apparatus, detracting from the user's athletic endeavor. Further, known designs fail to possess sufficient structural integrity to prevent re-injury of the knee joint as may be occasioned by impact to the knee joint during physical sport endeavors.

The features of the present invention are provided in recognition of the need for orthopedic braces and hinge streamlined, low profile, and easy to adjust while supporting joints and controlling and limiting joint movement. This recognition is realized with the invention described.

SUMMARY

According to various embodiments described in this disclosure, a hinge includes an upper hinge component, a lower hinge component, a first plate pivotally connected at a first location point to the upper hinge component and connected at a second location point to the lower hinge component, and a second plate pivotally connected at the first location point to the upper hinge component and at the second location point to the lower hinge component. A first rotation stop is connected at a third location point to the first and second plates. A center link is pivotally attached at a fourth location point to the upper hinge component and at a fifth location point to the lower hinge component. The center link has a first stop surface arranged to directly abut the first rotation stop. The hinge components and the center link are arranged between the first plate and the second plate.

The first rotation stop may be an extension stop. In a variation, the first rotation stop comprises a stop pin and a stop cover. The first stop surface and the first stop cover may have geometrically complementary surface shapes.

The hinge may be symmetrical regarding a central plane of rotation. The hinge may have a second rotation stop including a second stop pin and a second stop cover connected at a sixth location point to the first and second plates. The center link may have a second stop surface arranged to directly abut the second stop cover. The second stop surface and the second stop cover may have geometrically complementary surface shapes.

The connection of the center link at the fourth location point may rotate around the first location point and the connection of the center link at the fifth location point may rotate around the second location point. The upper hinge component and the lower hinge component may be in recesses of the center link.

The first plate may be identical to the second plate, and a cover may be secured to and located adjacent to the second plate.

In another embodiment, the hinge has an upper hinge component connected with a first pivoting connection to a first plate and a second plate, a lower hinge component connected with a second pivoting connection to the first plate and the second plate, a first rotation stop, and a center link connected with a third pivoting connection to the upper hinge component and a fourth pivoting connection to the lower hinge component. The center link abuts the first rotation stop at a predetermined hinge angle.

The upper hinge component, the lower hinge component, and the center link may be vertically aligned to have the same plane of rotation, and the center link and the first rotation stop may be arranged to apply symmetric loading of the hinge regarding the plane of rotation.

In another embodiment, the hinge includes an upper hinge component pivotally connected to a first plate at a first connection point, a lower hinge component pivotally connected to a second plate at a second connection point and pivotally connected to the first plate at a third connection point, and a rotation stop disposed between the upper hinge component and the lower hinge component and connected to the first plate at a fourth connection point.

The rotation stop may span a distance defined between the upper and lower hinge components.

In a variation, the rotation stop may define an interlocking extension stop and flexion stop, such that the extension and flexion stops interlock around the fourth connection point.

In another variation, the extension and flexion stops of the rotation stop interlock and span a distance between the upper and lower hinge components. In yet another variation, the extension and flexion stops interlock with one another at a forward end of the flexion stop and a rearward end of the extension stop. In yet another variation, the extension and flexion stops are contained between the outer plate and the inner plate.

A condyle plate may be secured to and located adjacent to the first plate. The condyle plate may have a retention area partially corresponding to the shape of the first plate. The condyle plate may have an enlarged opening at the third location point.

BRIEF DESCRIPTION OF THE DRAWINGS

The inventive hinge is described referring to the accompanying drawings that show preferred embodiments according to the device described. The device as disclosed in the accompanying drawings is illustrated for example only. The elements and combinations of elements described below and illustrated in the drawings can be arranged and organized differently to result in embodiments still within the spirit and scope of the device described.

DETAILED DESCRIPTION OF VARIOUS EMBODIMENTS

Figure 1:
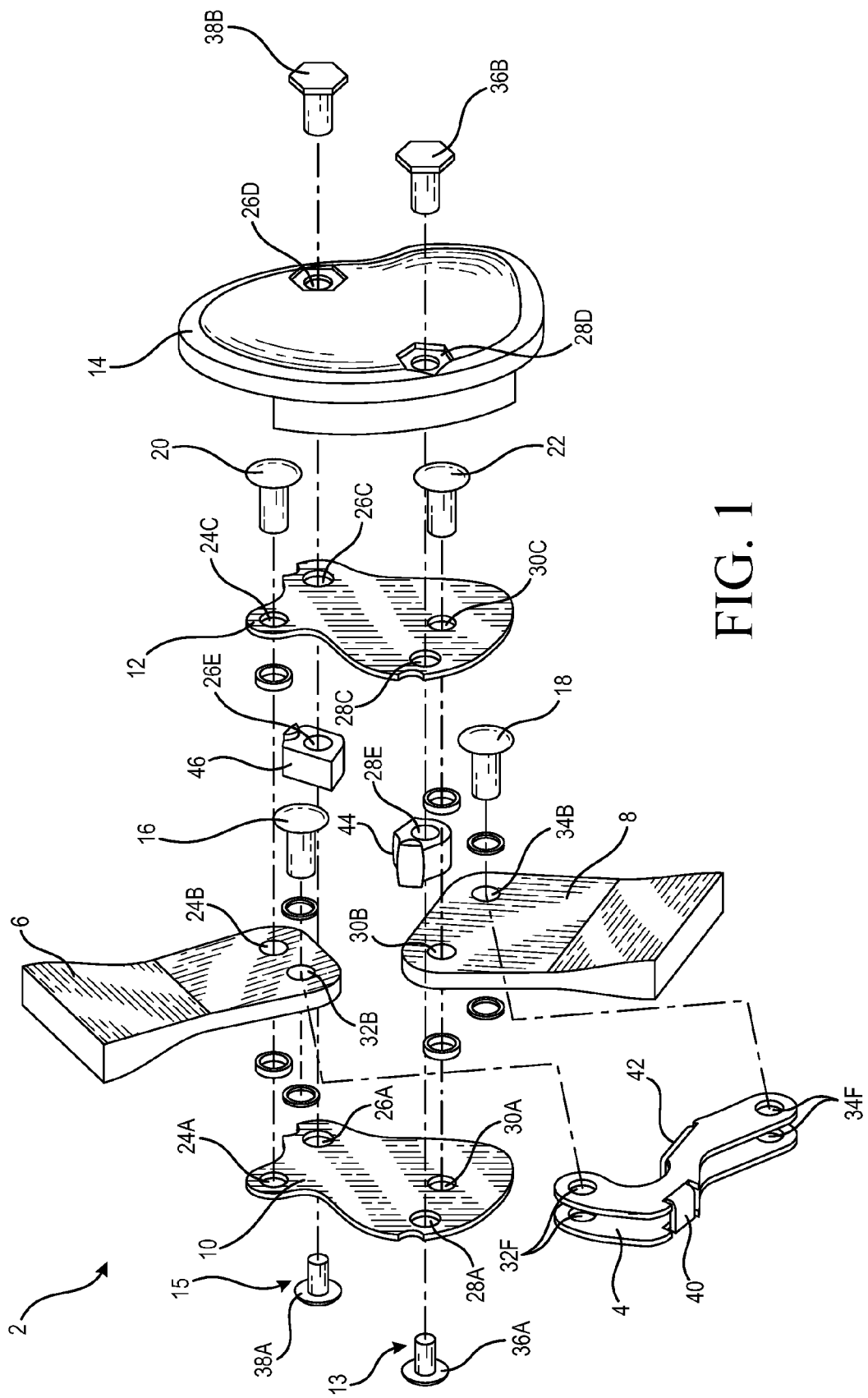
FIG. 1 is an exploded view of an embodiment of a hinge under the invention.

A better understanding of different embodiments of the invention may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. §112, paragraph 6.

Figure 3:
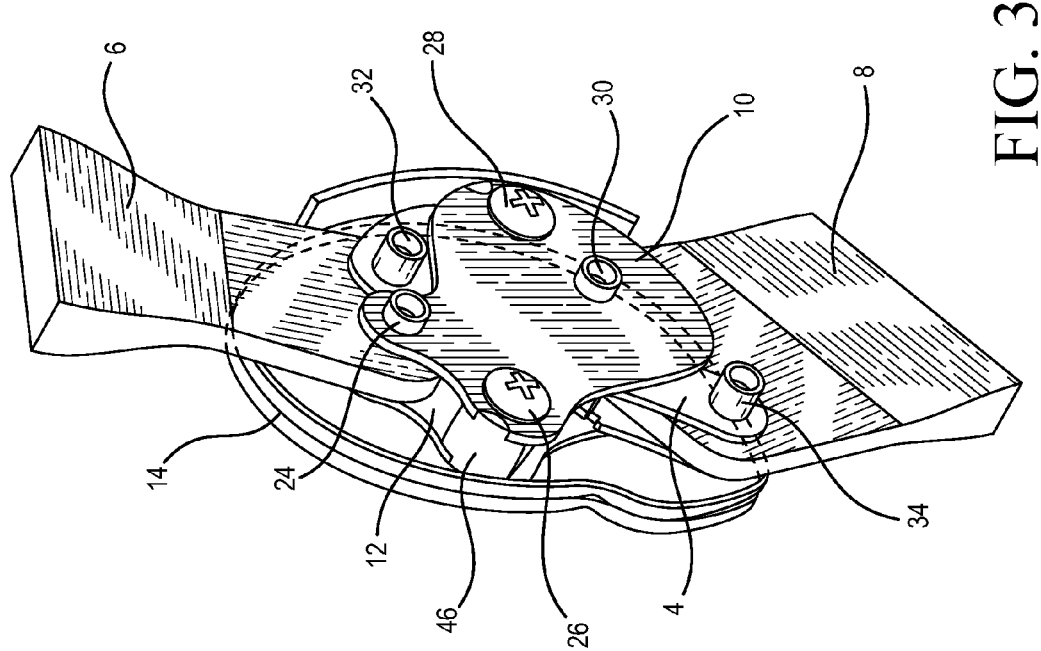
FIG. 3 shows an assembled view of the embodiment of FIG. 1.
Figure 2:
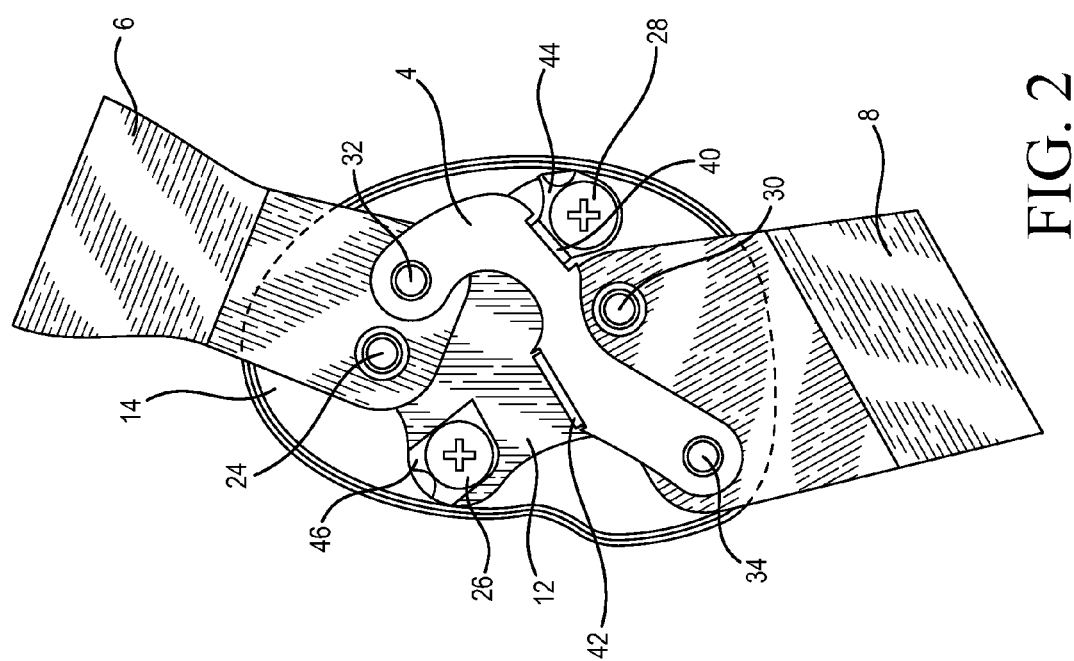
FIG. 2 is a side view of the embodiment of FIG. 1 with a hidden component to show the interior components.

FIGS. 1-3 show various views of a hinge embodiment 2 used in an orthopedic device such as a hinge of a knee brace in an extension position. FIG. 1 is an exploded view showing the components of the hinge 2. FIG. 2 is a side view of the hinge 2 with the plate 10 hidden to show the inner components of the hinge 2. FIG. 3 is another view of the hinge 2 including both plates 10, 12.

The hinge 2 can simulate the movement of the user's knee joint and limit flexion and extension of the knee joint within a certain range using a center link and rotation stops the center link 4 and the rotation stops 13, 15. The hinge 2 is symmetric regarding the central plane of rotation and advantageously distributes the loading of the rotation stops 13, 15 when a rotational limit has been reached symmetrically in the hinge to prevent the hinge arms 6, 8 from slipping sideways on the rotation stops. The slipping of the hinge arms 6, 8 may cause a bending moment in the hinge that would cause the failure of the hinge 2. The hinge 2 is further advantageous since the upper hinge arm 6 and the lower hinge arm 8 are connected to each other by the center link 4 and the inner and outer plates 10, 12 to provide additional support in the hinge to resist a bending moment in the hinge 2.

The loading of the rotation stops 13, 15 is distributed to the inner and outer plates 10, 12. FIGS. 1-3 also show a hinge cover 14 providing additional support to the rotation stops 13, 15. The rotation stops 13, 15 each comprises a stop pin 36, 38 and a stop cover 44, 46. By extending the stop pins 36, 38 through the inner and outer plates 10, 12 and the hinge cover 14, the rotation stop pins 36, 38 are supported by the plates 10, 12 and the hinge cover 14 when the center link 4 abuts a rotation stop. The center link 4 and the hinge arms 6, 8 are aligned along the central plane of rotation, and the inner and outer plates 10, 12 are parallel to the central plane of rotation which also acts as the plane of symmetry.

The flexion and extension of the hinge 2 as represented by the angle between the upper hinge arm 6 and the lower hinge arm 8 are limited by the extension stop 13 and the flexion stop 15. In this embodiment, a center link 4 connected between the upper and lower hinge arms 6, 8 is used to limit further rotation of the hinge arms 6, 8 in a specific direction. The stop pins 36, 38 also act as fasteners for the hinge 2 by extending through the entire hinge 2. The stop pins 36, 38 may be in a two-part screw 36A, 36B and 38A, 38B. The heads of parts 36B, 38B may have a geometric shape that fit into a corresponding recess on the cover 14 having the same geometric shape such that the heads are flush with the cover 14 as shown in FIG. 1. The cover 14 may also have a lip that extends over to plate 10 and along the length between the hinge arms 6, 8.

The extension stop pin 36 extends through an opening 28A of the inner plate 10, an opening 28C of the outer plate 12, and an opening 28D of the hinge cover 14 at the connection point 28. The flexion stop pin 38 extends through opening 26A of the inner plate 10, opening 26C of the outer plate 12, and opening 26D of the hinge cover 14 at the connection point 26. The stop pins 36, 38 are further provided with stop covers 44, 46 arranged to directly abut contact surfaces 40, 42 of the center link 4 to limit extension and flexion. The stop pins 36, 38 extend through apertures 28E, 26E, respectively. The stop covers 44, 46 may also have geometric shapes, which correspond to the shapes of the contact surfaces 40, 42, mostly if not fully engage the contact surfaces 40, 42 of the center link 4.

The rotation stops 36, 38 are prevented rotation of the upper and lower hinge arms 6, 8 at a predetermined angle defined by the geometrical shape and/or thickness of the stop covers 44, 46. The rotation stops 36, 38 are preferably perpendicular to the plane of rotation of the hinge arms 6, 8 and the center link 4. The extension and flexion of the hinge 2 can be adjusted by changing the shapes and/or thicknesses of the stop covers 44, 46. If the stop covers 44, 46 are not symmetrical around the center of the covers 44, 46, extensions may be on the plate sides of the covers 44, 46 that fit into a corresponding groove on the plates 10, 12 to lock the covers into position and prevent undesirable rotation of the stop covers. The stop covers 44, 46 preferably extend the distance between the plates 10, 12.

The center link 4 has the general shape of a hook and two central recesses into which the hinge arms 6, 8 are inserted. The center link 4 is attached at a first connection point 32 to the upper hinge arm 6 through openings 32F and aperture 32B of the upper hinge arm 6. A short rivet 16 is used to secure the upper hinge arm 6 pivotally to the center link 4 at the first connection point 32. Similarly, the center link 4 is attached at a second connection point 34 to the lower hinge arm 8 through openings 34F and a through bore 34B of the lower hinge arm. A short rivet 18 is used to secure the lower hinge arm 8 pivotally to the center link 4 at the second connection point 34. The short rivets 16, 18 and the stop pins 36, 38 may have washers between components to properly align, space, and fasten the individual components of the hinge 2.

As shown in FIGS. 1-3, the center link 4 rotates around two points 24, 30 and around the edges of the inner and outer plates 10, 12. The lower hinge arm 8 is preferably wider than the upper hinge arm 6 to provide a larger rotational radius for the lower end of the center link 4. By using the center link 4, which is attached to both hinge arms 6, 8, as the contact point with the rotation stops 36, 38, a stronger rotation stopping contact is formed with less opportunity for the hinge arms 6, 8 to slip and allow further undesirable flexion or extension beyond the stopping points.

The inner and outer plates 10, 12 are on either side of the center link 4 and are connected to the upper hinge arm 6 at a connection point 24 and to the lower hinge arm 8 at a connection point 30. The outer plate 12 fits within a recess of the hinge cover 14 and has at least two contact points with the outer plate 12 along the edge of the hinge cover 14. Preferably, the contact points are located near the connection points 26, 28.

The length of the hinge arms 6, 8 may be changed to adjust the center of rotation of the hinge to create non-natural kinematics to correct for ACL or PCL deficient knees. The hinge 2 can also be used with a spring-type center link to adjust the level of correction. A rack and pinion gear system may be used with the center link and the hinge arms.

Figure 4:
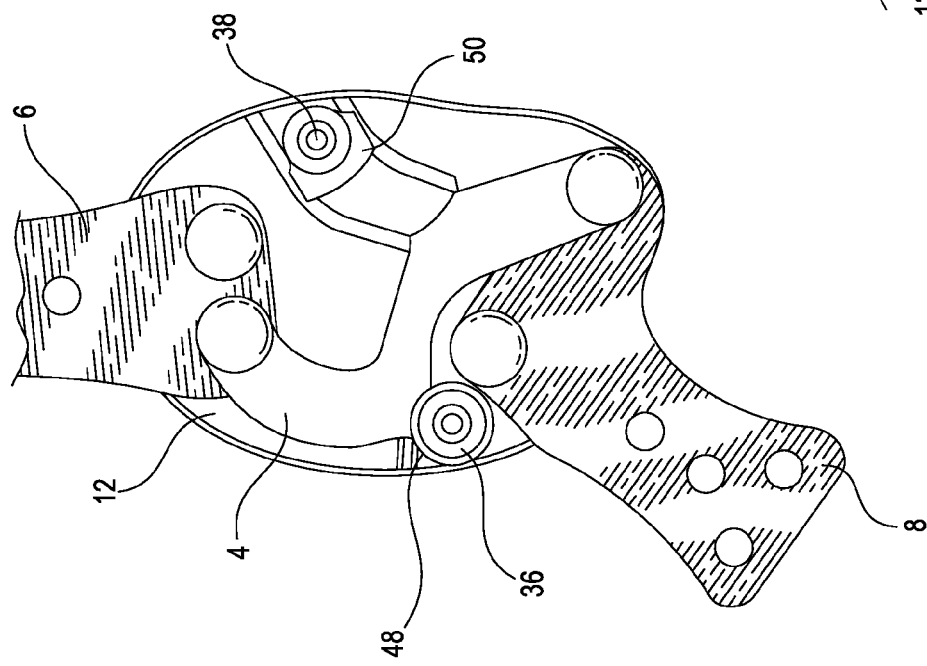
FIG. 4 shows an embodiment of the rotation stop covers.

FIG. 4 shows an embodiment of the covers 44, 46. The extension stop cover 48 has a cylindrical shape, and the flexion stop cover 50 has a partially curved surface. The center link 4 in this embodiment is provided with curved contact surfaces corresponding to the surface shape of the stop covers 48, 50.

The geometrical surface shape of the stop covers in combination with the thickness of the stop covers and the geometrical shape of the contact surfaces 40, 42 of the center link 4 determine the stopping angles of the upper hinge arm and the lower hinge arm.

Figure 5:
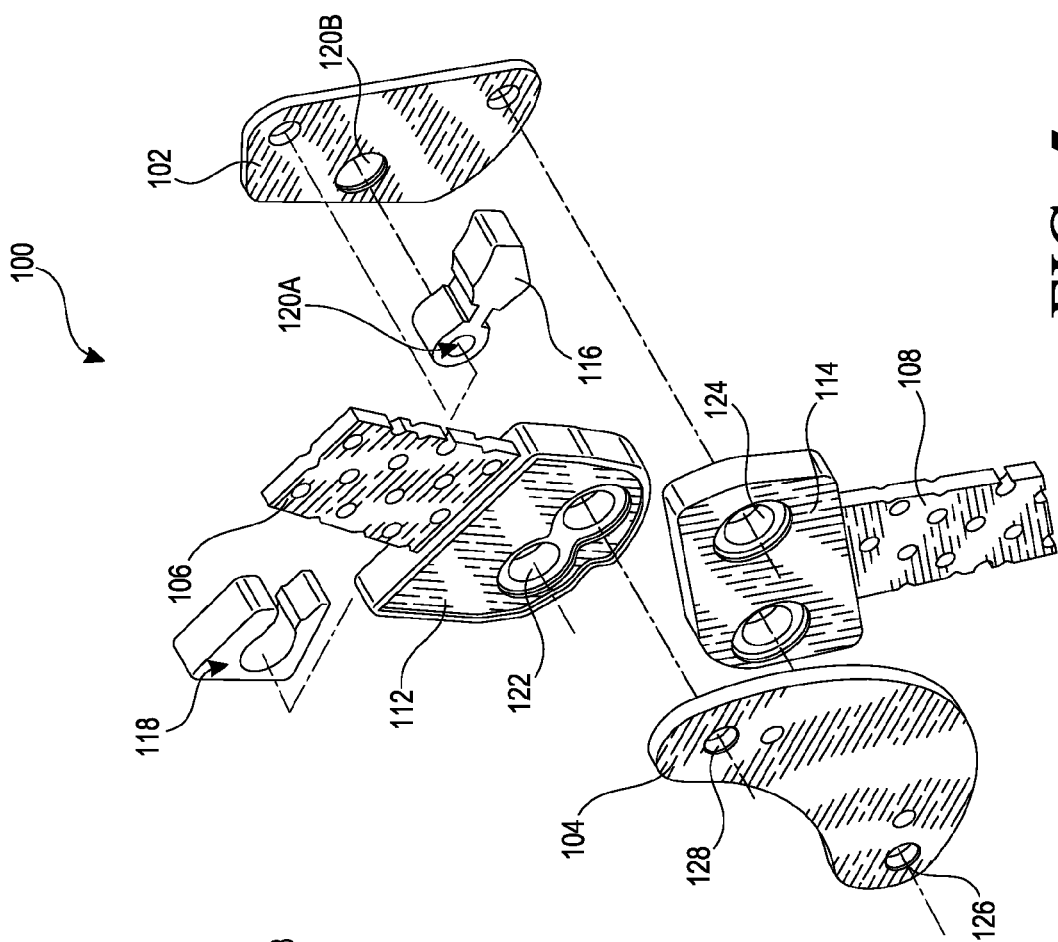
FIG. 5 shows an exploded view of another embodiment of the hinge.
Figure 6:
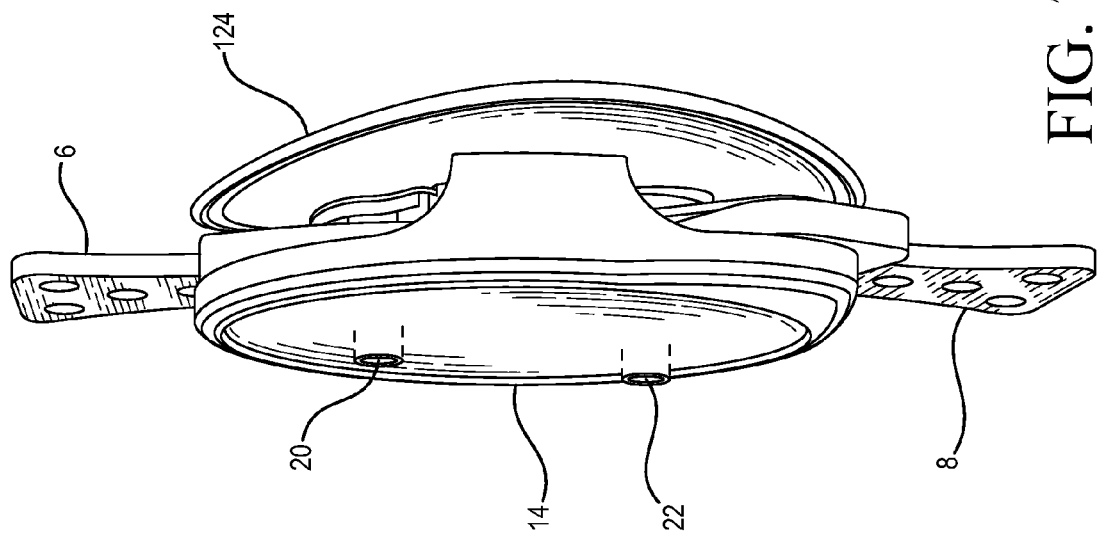
FIG. 6 is a side view of the embodiment of FIG. 5.

In another embodiment illustrated in FIGS. 5 and 6, the hinge 100 is asymmetric regarding the plane of rotation. The hinge 100 may be the hinge described in application Ser. No. 12/877,429 published as U.S. publication number 2012/0059296, hereby incorporated by reference.

The hinge 100 similarly has an inner plate 102, an outer plate 104, upper hinge arm 106, lower hinge arm 108, and a rotation stop 110. The upper hinge arm 106 has a hinge arm cover 112 at its lower end, and the lower hinge arm 108 has a hinge arm cover 114 at its upper end. The upper hinge arm 106 is pivotally connected to the inner plate 102 at a connection point 122 and the outer plate 104 at a connection point 128. The lower hinge arm is connected to the inner plate 102 at a connection point 124 and the outer plate 104 at a connection point 126.

In this embodiment, the limiting of rotation is achieved when the hinge arm covers 112, 114 abut the rotation stop 110 to limit extension and flexion. The top of the rotation stop 110 has a geometric shape corresponding to the shape of the bottom of the hinge cover 112. The bottom of the rotation stop 110 has a geometric shape corresponding to the shape of the top of the hinge cover 114.

The rotation stop 110 may comprise two components for flexion and extension stops. An extension stop 116 is attached at a connection point 120 to the inner plate 102. A flexion stop 118 interlocks over the connection end of the extension stop 116. Since the rotation stop 110 requires only a single connection point, there is less opportunity for the extension stop 116 and the flexion stop 118 to disconnect from each other when a rotational limit is reached. The degree to which rotation is limited may be adjusted by changing the size and/or shape of the extension stop 116 or the flexion stop 118.

Figure 7:
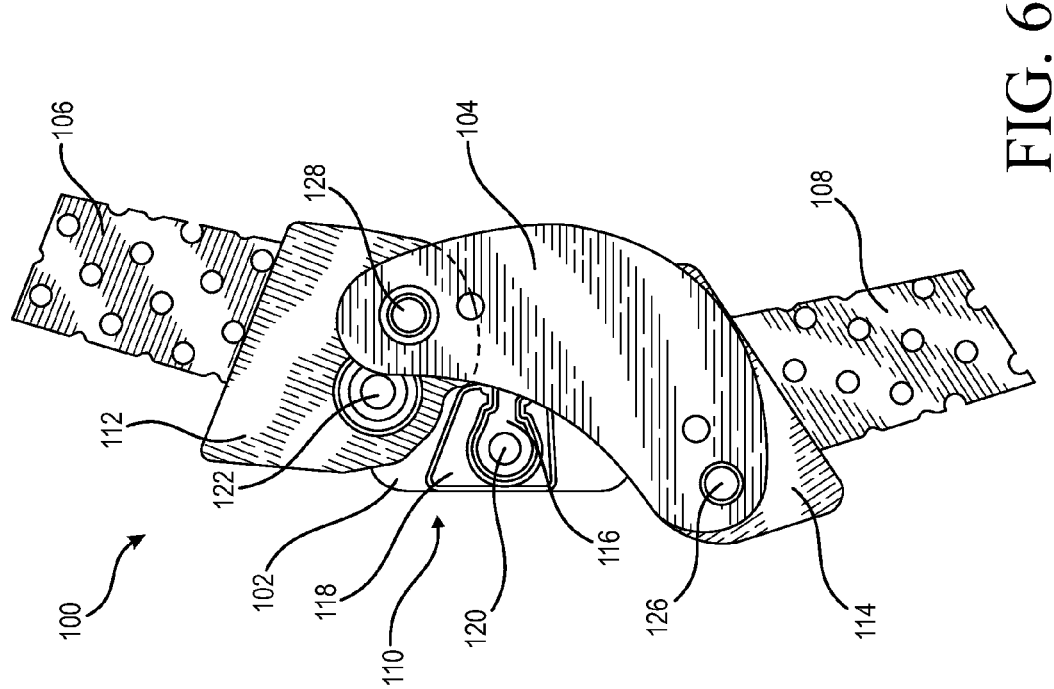
FIG. 7 is a view from the posterior of another embodiment of the hinge showing a hinge cover and a condyle plate.
Figure 8:
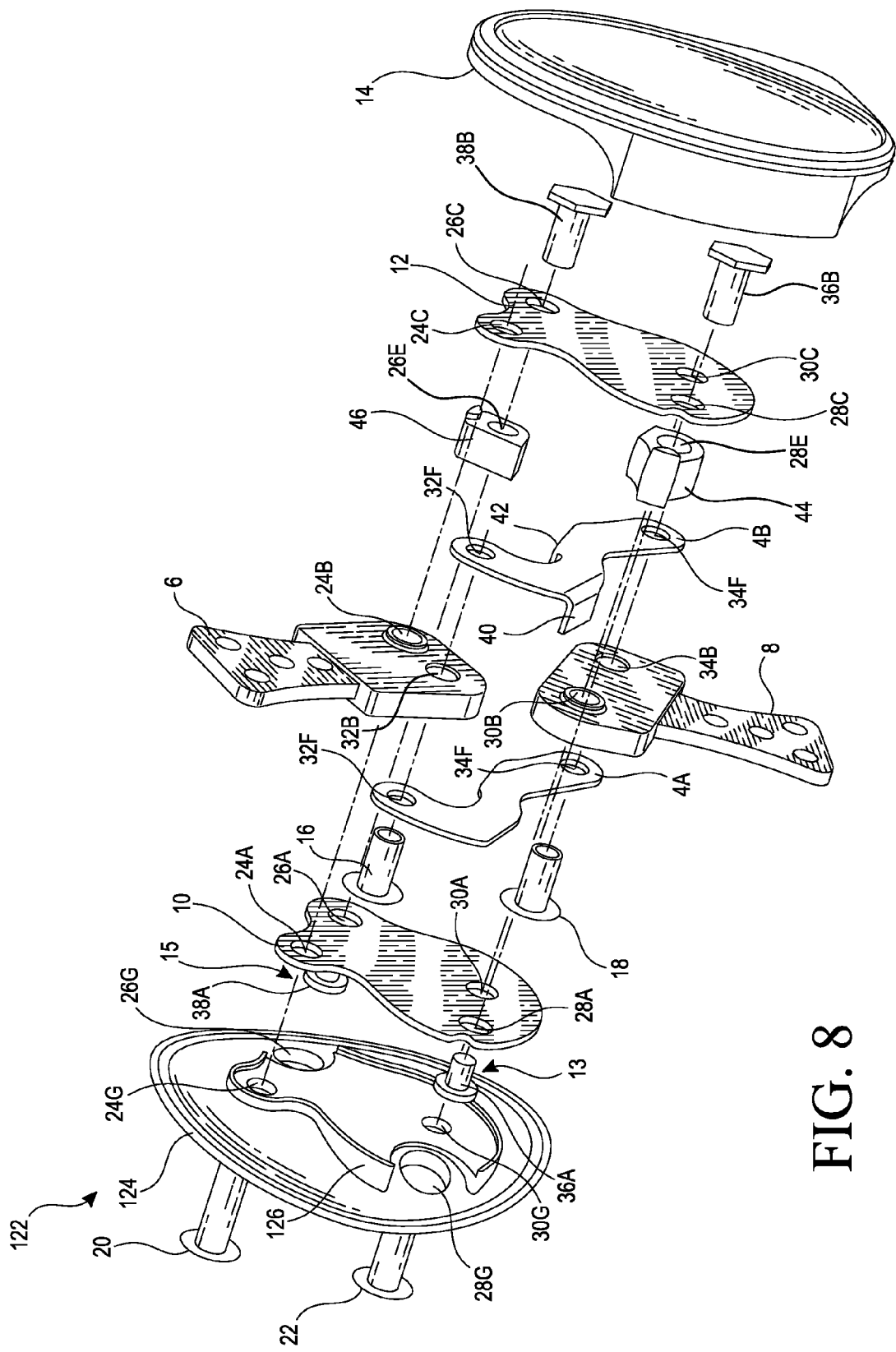
FIG. 8 is an exploded view of the embodiment in FIG. 7.

FIG. 7 illustrates another embodiment of the hinge 122, and FIG. 8 is an exploded view of the hinge 122. The hinge 122 is largely similar to the hinge 2, and the same reference numerals are used for components in the hinge 122 similar to those of the hinge 2.

The hinge 122 includes the upper hinge arm 6, lower hinge arm 8, the inner and outer plates 10, 12, the center links 4A, 4B, the extension stops 13, 15, connectors 16, 18, 20, 22 used with the upper and lower hinge arms 6, 8, and the hinge cover 14. The hinge 122 further includes a condyle plate 124. The condyle plate 124 and the hinge cover 14 are in more detail in the exploded view of the hinge 122 in FIG. 8.

The condyle plate 124 provides support to the condyle region of the knee and is preferably made from a resilient material such that the condyle plate 124 can flex slightly during movement of the knee. The condyle plate 124 further has a slightly curved shape to follow the general surface shape of the knee. A retention area 126 is on hinge side of the condyle plate 124. The retention area 126 is shaped such that the inner plate 10 is form fitted in the retention area 126. As shown in FIG. 8, the retention area 126 largely outlines the shape of the inner plate except for the area around the rotation stops 13, 15. The retention area 126 has a cut out near the area of the rotation stops 13, 15.

The embodiments of the hinge are advantageous in that the degree to which flexion and extension of the knee is limited are easily and quickly adjustable. In this respect, the condyle plate has enlarged openings 26G, 28G to allow easy access to the stop pins 38A, 36A to remove or exchange stop covers 46, 44 which determine the degree to which the knee may be extended or flexed.

In the interest of equally distributing load exerted on the hinge 122, the rotation stops 13, 15 may extend from the inner plate 10 through the hinge cover 14. The condyle plate 124 also provides support for the inner plate 10 since the retention area 126 is form fitted around the inner plate 10. Alternatively, the hinge cover 14 may have internal recesses in the interior side of the hinge to receive the end of rotation stop pins 36B, 38B.

Long rivets 20, 22 at connection points 24A, 24B, 24C, 24G, 30A, 30B, 30C, 30G extend through the condyle plate 124 and the hinge cover 14 to firmly secure the condyle plate and the hinge cover 14 to the hinge components. An indicia element such as a sticker may be placed over the hinge cover 14 to cover the long rivets 20, 22 for aesthetic and protection purposes so that the long rivets 20, 22 are not exposed on the outer surface of the hinge 122.

The hinge cover 14 of the hinge 122 includes two lips to shield the anterior and posterior side of the hinge from external particles and to prevent material from becoming trapped in the interior of the hinge 122 by filling in the clearance between the hinge cover 14 and the condyle plate 124. The first lip extends from the hinge cover 14 and the condyle plate 124 on the anterior side and is similar to the lip on the hinge cover 14 of the hinge 2. The second lip illustrated in FIG. 7 is on the posterior side of the hinge and extends from the hinge cover 14 to the condyle plate 124. The lips have a length corresponding to length of the clearance between the upper and lower hinge arms 6, 8 at full extension or flexion of the hinge 122.

While the foregoing embodiments have been described and shown, alternatives and modifications of these embodiments, such as those suggested by others may be made to fall within the scope of the invention. While the hinge has been described in combination with a knee brace, it will be understood that the principles described may be extended to other types of orthopedic and prosthetic devices.

The invention claimed is:

1. A hinge, comprising:
an upper hinge component;
a lower hinge component;
a first plate pivotally connected at a first location point to the upper hinge component and connected at a second location point to the lower hinge component;
a second plate pivotally connected at the first location point to the upper hinge component and at the second location point to the lower hinge component;
a first rotation stop connected at a third location point to the first and second plates; and
a center link has a first end pivotally attached at a fourth location point to the upper hinge component and a second end pivotally attached at a fifth location point to the lower hinge component, the center link having a first stop surface arranged to directly abut the first rotation stop;
wherein the hinge components and the center link are arranged between the first plate and the second plate;
wherein the first stop surface is located solely between the fourth and fifth location points.

2. The hinge according to claim 1, wherein the first rotation stop comprises a stop pin and a stop cover.

3. The hinge according to claim 2, wherein the first stop surface and the first stop cover have geometrically complementary surface shapes.

4. The hinge according to claim 1, further comprising: a second rotation stop including a second stop pin and a second stop cover connected at a sixth location point to the first and second plates, wherein the center link has a second stop surface arranged to directly abut the second stop cover.

5. The hinge according to claim 4, wherein the second stop surface and the second stop cover have geometrically complementary surface shapes.

6. The hinge according to claim 1, wherein the first rotation stop is an extension stop.

7. The hinge according to claim 1, wherein the hinge is symmetrical regarding a central plane of rotation.

8. The hinge according to claim 1, wherein the connection of the center link at the fourth location point rotates around the first location point and the connection of the center link at the fifth location point rotates around the second location point.

9. The hinge according to claim 1, wherein the upper hinge component and the lower hinge component are in recesses of the center link.

10. The hinge according to claim 1, wherein the first plate is identical to the second plate.

11. The hinge according to claim 1, further comprising a cover secured to and located adjacent to the second plate.

12. The hinge according to claim 1, further comprising: a condyle plate secured to and located adjacent to the first plate.

13. The hinge according to claim 1, wherein a condyle plate has a retention area partially corresponding to a shape of the first plate.

14. The hinge according to claim 1, wherein a condyle plate has an enlarged opening at the third location point.

15. The hinge according to claim 1, wherein the first stop surface is located along only a first side of the center link.

16. The hinge according to claim 1, wherein the center link defines a second stop surface arranged to directly abut a second rotation stop, and located on an opposite side of the center link to the first stop surface.

17. The hinge according to claim 1, wherein the center link defines a non-linear profile including a curvature between the fourth and fifth location points.

18. The hinge according to claim 1, wherein the first stop surface is substantially flat and the first stop cover has geometrically complementary surface shapes to the first stop surface.

19. A hinge, comprising:
an upper hinge component connected with a first pivoting connection to a first plate and a second plate;
a lower hinge component connected with a second pivoting connection to the first plate and the second plate;
a first rotation stop; and
a center link connected with a third pivoting connection to the upper hinge component and a fourth pivoting connection to the lower hinge component, the center link abutting the first rotation stop at a predetermined hinge angle, the center link defining a substantially flat first stop surface arranged to directly abut the first rotation stop and located solely between the third and fourth pivoting connections;
wherein the upper hinge component, the lower hinge component, and the center link are vertically aligned to have the same plane of rotation, and
wherein the center link and the first rotation stop apply symmetric loading of the hinge regarding the plane of rotation.

20. A hinge, comprising:
an upper hinge component;
a lower hinge component;
a first plate pivotally connected at a first location point to the upper hinge component and connected at a second location point to the lower hinge component;
a second plate pivotally connected at the first location point to the upper hinge component and at the second location point to the lower hinge component;
a first rotation stop connected at a third location point to the first and second plates; and
a center link pivotally attached at a fourth location point to the upper hinge component and at a fifth location point to the lower hinge component, the center link forming a substantially flat first stop surface arranged to directly abut the first rotation stop and located solely between the fourth and fifth location points along a first side of the center link;

wherein the hinge components and the center link are arranged between the first plate and the second plate.

* * * * *